(12) United States Patent
Takahashi

(10) Patent No.: US 8,758,319 B2
(45) Date of Patent: Jun. 24, 2014

(54) ABSORBENT PRODUCT

(75) Inventor: Yuki Takahashi, Mima-gun (JP)

(73) Assignee: Livedo Corporation, Ehime (JP)

( * ) Notice: Subject to any disclaimer, the term of this patent is extended or adjusted under 35 U.S.C. 154(b) by 469 days.

(21) Appl. No.: 12/873,448

(22) Filed: Sep. 1, 2010

(65) Prior Publication Data

US 2011/0066128 A1 Mar. 17, 2011

(30) Foreign Application Priority Data

Sep. 17, 2009 (JP) ................................ P2009-216144

(51) Int. Cl.
*A61F 13/00* (2006.01)
*A61F 13/494* (2006.01)

(52) U.S. Cl.
CPC .................................. *A61F 13/4942* (2013.01)
USPC ................................ 604/385.28; 604/385.26

(58) Field of Classification Search
CPC ............ A61F 13/494; A61F 13/49406; A61F 13/49413; A61F 13/4942; A61F 13/49426; A61F 13/49446; A61F 13/475; A61F 13/4751; A61F 13/4752; A61F 13/4753
USPC ............. 604/385.25, 385.26–385.28, 385.21, 604/385.29, 385.101
See application file for complete search history.

(56) References Cited

U.S. PATENT DOCUMENTS

| | | | | |
|---|---|---|---|---|
| 5,931,826 A * | 8/1999 | Faulks et al. | ............. | 604/385.27 |
| 6,562,017 B1 * | 5/2003 | Nakaoka et al. | ......... | 604/385.28 |
| 7,462,174 B2 * | 12/2008 | Nishitani et al. | ......... | 604/385.27 |
| 2003/0093056 A1 * | 5/2003 | Kurata | .................. | 604/385.101 |
| 2005/0067083 A1 | 3/2005 | Vergona | | |
| 2005/0182380 A1 * | 8/2005 | Fujioka et al. | ........... | 604/385.28 |
| 2006/0206090 A1 | 9/2006 | Mori | | |
| 2007/0073259 A1 * | 3/2007 | Erdman et al. | ........... | 604/385.28 |
| 2007/0088309 A1 * | 4/2007 | Ehrnsperger et al. | ..... | 604/385.28 |
| 2007/0149943 A1 * | 6/2007 | Miyamoto | ............... | 604/385.28 |
| 2010/0292663 A1 * | 11/2010 | LaVon et al. | .................. | 604/367 |

FOREIGN PATENT DOCUMENTS

| | | |
|---|---|---|
| CN | 2601646 | 2/2004 |
| CN | 101287433 | 10/2008 |
| EP | 1 312 327 | 5/2003 |
| JP | 9-271489 | 10/1997 |
| JP | 2003-210521 | 7/2003 |
| JP | 2006-223881 | 8/2006 |
| JP | 2008-154606 | 7/2008 |
| JP | 2008-289602 | 12/2008 |
| WO | 2007/043028 | 4/2007 |

OTHER PUBLICATIONS

Extended European Search Report (in English language) issued Jun. 10, 2011 in corresponding European Patent Application No. 10 00 9003.

* cited by examiner

*Primary Examiner* — Lynne Anderson
*Assistant Examiner* — Bradley Philips
(74) *Attorney, Agent, or Firm* — Wenderoth, Lind & Ponack, L.L.P.

(57) ABSTRACT

In a standing part (342) of each side wall part (34) in an absorbent product (1), an inwardly bending part (3423) is formed between a first elastic member (35) and a second elastic member (36). When the absorbent product (1) is worn, the inwardly bending part (3423) where no elastic member is provided comes into contact with a wearer to be deformed into surface shape, and a portion in the vicinity of the inwardly bending part (3423) and the first elastic member (35) contacts with the wearer in surface shape. Therefore, the wearer is prevented from being compressed excessively by the first elastic member (35) and the second elastic member (36) and excrement is prevented from leaking out to the outer side of the absorbent product (1).

14 Claims, 4 Drawing Sheets

ABSORBENT PRODUCT

TECHNICAL FIELD

The present invention relates to an absorbent product for receiving excrement from a wearer.

BACKGROUND ART

In an absorbent product, such as a disposable diaper, for receiving excrement from a wearer, a pair of side wall parts is conventionally provided on both sides in a width direction, and elastic yarns or the like provided on each side wall part contract to make the side wall part stand up toward the wearer. When the absorbent product is worn, the pair of side wall parts becomes standing gathers which contact with the vicinity of wearer's groin, and therefore, leakage of excrement from the absorbent product is prevented.

Japanese Patent Application Laid-Open No. 2006-223881 (Document 1) discloses a paper diaper where elastic extensible members for contact are provided at a distal edge (free edge) of each barrier cuff, elastic extensible members for standing are provided at a proximal edge, and the barrier cuff is standing almost vertically by high contractive force of the elastic extensible members for standing. Thus, in the case where an auxiliary pad is located at the inner side of the paper diaper, the auxiliary pad is wrapped around with the barrier cuffs which are not laid down and retroflex.

In a disposable diaper disclosed in Japanese Patent Application Laid-Open No. 9-271489 (Document 2), each of two flaps provided on both side portions of an absorber has a base terminal part fixed on the absorber, a free terminal part on which elastic body is attached, and a turn-out line formed between the base terminal part and the free terminal part. A portion between the base terminal part and the turn-out line in the flap extends outward and upward with increasing distance from the base terminal part, and a portion between the turn-out line and the free terminal part extends inward and upward with increasing distance from the turn-out line. In the disposable diaper of Document 2, since the flap is made to project outward while standing up as above, a pocket structure having large capacity is formed.

Japanese Patent Application Laid-Open No. 2008-154606 (Document 3) discloses an absorbent product where side leakage prevention parts whose bodies are hollow are provided on both side portions of an absorber and string-like elastic members each extending in a longitudinal direction are provided at the top of each side leakage prevention part. The hollow body of side leakage prevention part is formed by curving a band-like nonwoven fabric at a curve part along the longitudinal direction and bonding end parts on both sides of the curve part to the upper surface and lower surface of the absorber, respectively.

In an absorbent product such as the paper diaper of Document 1 or the disposable diaper of Document 2, since the free edge of each barrier cuff or each flap contacts with the wearer in linear shape, (skin of) the wearer is compressed excessively (tightly) by the elastic member provided at the free edge and comfort level of the wearer decreases.

In the absorbent product of Document 3, since the side leakage prevention part is hollow, compression to the wearer by the elastic member provided on the side leakage prevention part is reduced to a certain level. However, since the elastic member is provided at the top of side leakage prevention part which is the closest portion to the wearer in the side leakage prevention part, the issue where the wearer is compressed excessively by the elastic member remains unsolved.

In addition, manufacturing process of the absorbent product of Document 3 becomes complicated, because the both end parts of nonwoven fabric curved as described above need be bonded to the upper surface and lower surface of the absorber without collapsing the space formed by curving.

SUMMARY OF INVENTION

The present invention is intended for an absorbent product for receiving excrement from a wearer. It is an object of the present invention to prevent the wearer from being compressed excessively by an elastic member in each side wall part preventing leakage of excrement.

The absorbent product according to the present invention comprises: a sheet-like main body part where an absorbent core is located between a back sheet and a top sheet; and a pair of side wall parts which is located on both side portions of the main body part and which extends in a longitudinal direction of the main body part, wherein each side wall part comprises: a standing part standing up from the main body part at a middle portion of the each side wall part in the longitudinal direction; two side wall end parts which are both end portions of the each side wall part in the longitudinal direction, being fixed on the main body part; and an elastic member which is bonded to a free edge of the standing part along the free edge and which contracts to form gathers in the standing part; and each side wall end part comprises: a first fixed part which is continuous in the longitudinal direction from a portion of the standing part, the portion being in the vicinity of a fixed edge of the standing part, the first fixed part lying inward to be fixed to the main body part; and a second fixed part lying between the main body part and the first fixed part to be fixed to the main body part and spreading outward from an inside edge of the first fixed part.

In the present invention, it is possible to prevent the wearer from being compressed excessively by the elastic member in each side wall part preventing leakage of excrement.

According to a preferred embodiment of the present invention, the each side wall part further comprises another elastic member which is bonded to the standing part in almost parallel with the longitudinal direction at a position away from the free edge and which contracts to form gathers in the standing part, and an inwardly bending part is formed in the standing part at a position between the elastic member and the another elastic member. In this absorbent product, since a portion located on the inside of the another elastic member in the standing part contacts with the wearer in surface shape (surface-like shape), it is possible to more certainly prevent the wearer from being compressed excessively and to prevent leakage of excrement more certainly.

In this case, preferably the another elastic member is a plurality of elastic elements each extending in the longitudinal direction which are arranged in a direction orthogonal to the longitudinal direction. Thus, a portion on which the another elastic member is located becomes surface shape and has high stiffness, and therefore the inwardly bending part is clearly formed. As the result, it is possible to easily keep the portion of standing part in surface shape where the portion contacts with the wearer.

More preferably, a portion of the standing part being in the vicinity of the free edge is in almost parallel with the main body part, or the portion is inclined so as to come closer to the main body part toward the free edge. This can more certainly prevent the wearer from being compressed excessively by the elastic member.

According to an aspect of the present invention, since the elastic member is a plurality of elastic elements each extending in the longitudinal direction which are arranged in a direction orthogonal to the longitudinal direction, the portion of the standing part being in the vicinity of the free edge can more easily be formed in surface shape.

According to another aspect of the present invention, a pair of side sheets is located on the both side portions of the main body part, each side sheet comprises a strip-like bonded part bonded on the main body part, the each side wall part is a portion of the each side sheet and is continuous from the bonded part, and the each side sheet further comprises an elastic member which is bonded thereto along the fixed edge of the standing part.

In addition, there may be a case where an auxiliary absorbent pad is located on the main body part at a position between the pair of side wall parts, and each side portion of the auxiliary absorbent pad is located between the standing part of the each side wall part and the main body part.

These and other objects, features, aspects and advantages of the present invention will become more apparent from the following detailed description of the present invention when taken in conjunction with the accompanying drawings.

DESCRIPTION OF EMBODIMENTS

Figure 1:
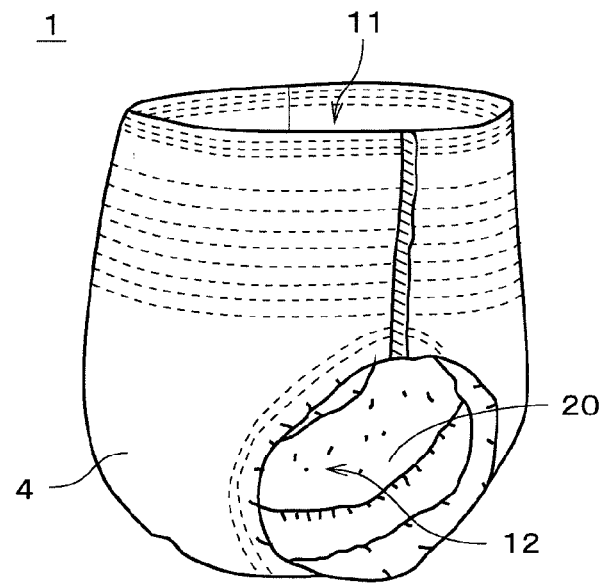
FIG. 1 is a perspective view showing appearance of an absorbent product.

FIG. 1 is a perspective view showing appearance of an absorbent product 1 in accordance with a preferred embodiment of the present invention. As shown in FIG. 1, the absorbent product 1 is a pants-type (i.e., pull-up type) disposable diaper which has a waist opening 11 at an upper end being an end on the upper side of FIG. 1 and a pair of leg openings 12 on a lower part, and it receives excrement from a wearer.

Figure 2:
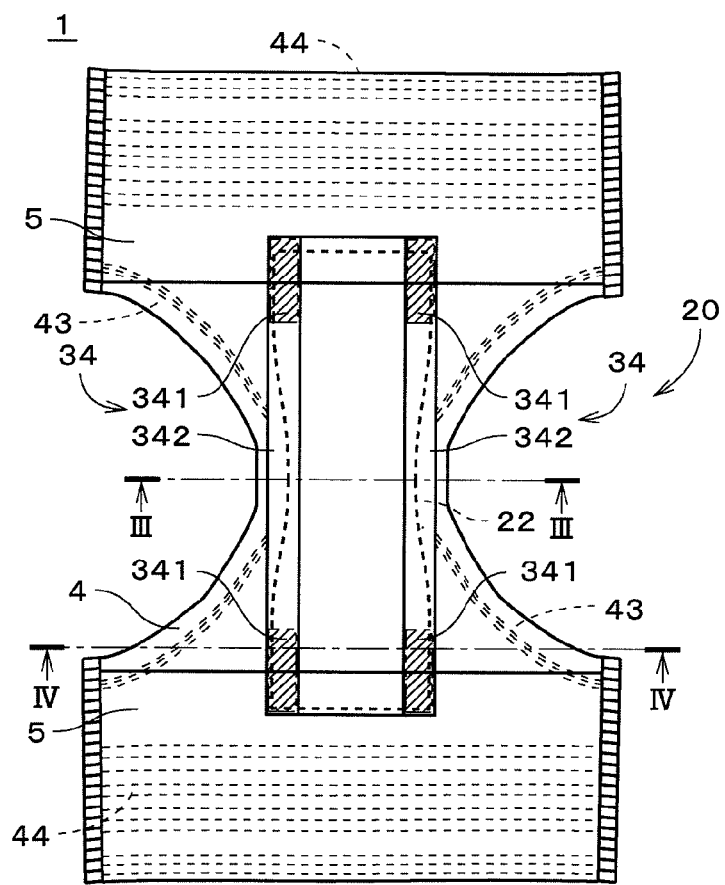
FIG. 2 is a plan view of the absorbent product in a state where the absorbent product is developed.

FIG. 2 is a plan view of the absorbent product 1 in a state where the absorbent product 1 is developed and in FIG. 2, the absorbent product 1 is viewed from the wearer's side. As shown in FIG. 2, the absorbent product 1 has an outer covering sheet 4, an almost sheet-like absorber 20 which is attached on the outer covering sheet 4 to absorb excrement from the wearer (i.e., the absorber 20 is located on the wearer's side of the outer covering sheet 4), and two end holding sheets 5 which are bonded to the outer covering sheet 4 at both ends of absorber 20 in its longitudinal direction (i.e., an up-down direction in FIG. 2). Each end portion of absorber 20 in the longitudinal direction is caught between the end holding sheet 5 and the outer covering sheet 4 to be fixed.

In the absorbent product 1, a lower portion in FIG. 2 is to be positioned on the front side (stomach side) of the wearer, and an upper portion in FIG. 2 is to be positioned on the back side of the wearer. In the following description, the portions of the absorbent product 1 which are to be positioned on the front side and the back side of the wearer are referred to as a "front part" and a "back part", respectively, and a portion to face a crotch region of the wearer at a position between the front part and the back part is referred to as a "middle part".

As shown in FIG. 1, in the absorbent product 1, the outer covering sheet 4 is folded at the middle part together with the absorber 20. In the state where the middle part is located on the downside, right and left ends of the front part (i.e., both ends in a width direction orthogonal to the longitudinal direction) are bonded to right and left ends of the back part, respectively. Therefore, the waist opening 11 is formed at upper ends of the front part and the back part, and on the downside of the front part and the back part, the pair of leg openings 12 is formed on right and left sides of the middle part, to thereby form the absorbent product 1 in a shape of underpants.

Figure 3:
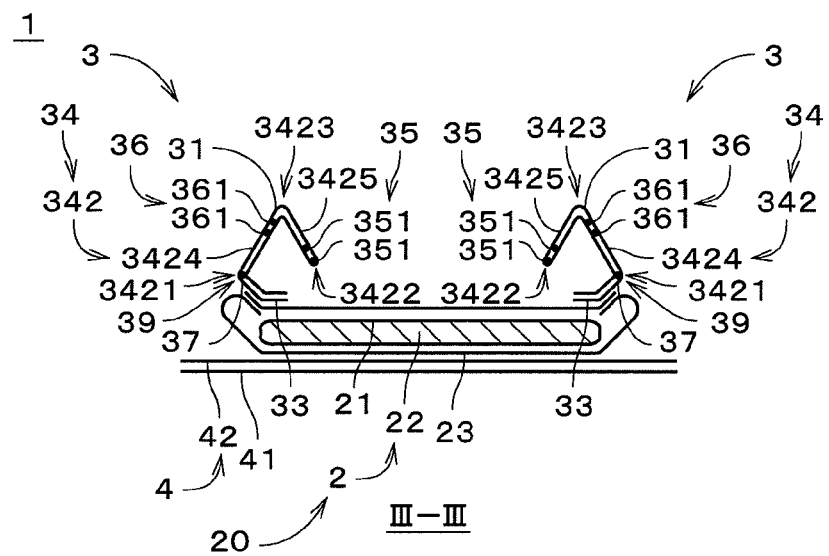
FIGS. 3 and 4 are cross-sectional views of the absorbent product.
Figure 4:
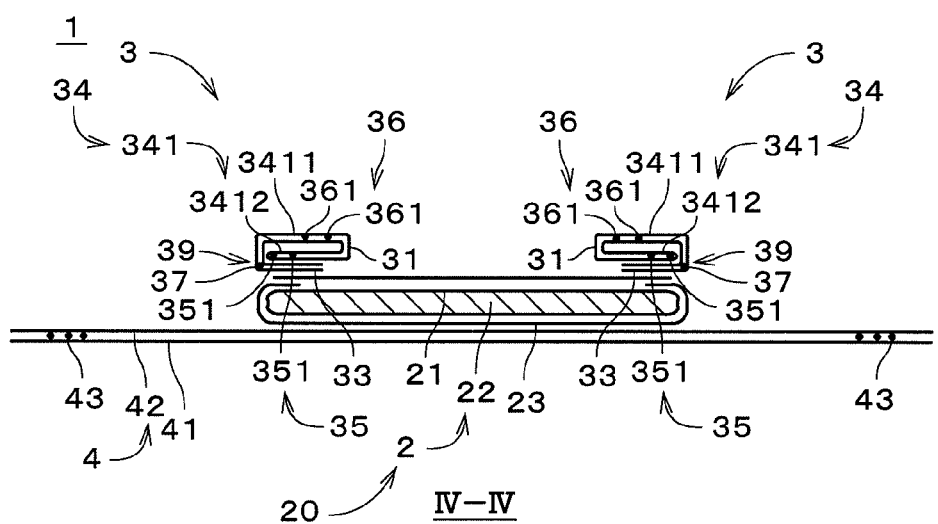

FIGS. 3 and 4 are cross-sectional views of the absorbent product 1 taken along lines and IV-IV in FIG. 2 (i.e., cross-sectional views at the middle part and the front part), respectively. In FIGS. 3 and 4, respective constituents of the absorbent product 1 are drawn to be slightly apart from one another for easy understanding of the drawings. A structure of the back part is similar to the structure of the front part shown in FIG. 4. The absorber 20 has a sheet-like main body part 2 and a pair of side sheets 3 located on both side portions of the main body part 2 (i.e., both sides of the main body part 2 in the width direction), and the pair of side sheets 3 extends across almost the entire length of the main body part 2 in the longitudinal direction. The main body part 2 has a top sheet 21, a back sheet 23 and an absorbent core 22 which is located between the top sheet 21 and the back sheet 23. The contour of the absorbent core 22 is drawn by thick broken lines in FIG. 2 for easy understanding of the drawing. As shown in FIG. 2, a width of the absorbent core 22 at each of both ends in the longitudinal direction is larger than that at middle in the longitudinal direction. In other words, the absorbent core 22 is formed in a form of hourglass.

As shown in FIGS. 3 and 4, each side sheet 3 has a side sheet main body 31, and a first elastic member 35, a second elastic member 36 and a third elastic member 37 which are bonded to the side sheet main body 31 with hot melt adhesive or the like. The first elastic member 35 is bonded to a free edge (a free end) of the side sheet main body 31 along the free edge, and the second elastic member 36 and the third elastic member 37 are bonded to the side sheet main body 31 at positions away from the free edge. The first elastic member 35 is two first elastic elements 351 which are string-like and each of which extends in the longitudinal direction, and the second elastic member 36 is two second elastic elements 361 which are string-like and each of which extends in the longitudinal direction. The third elastic member 37 is one elastic element which is string-like and which extends in the longitudinal direction.

The outer covering sheet 4 has a first covering sheet 41 and a second covering sheet 42, and as shown in FIG. 2, it also has leg elastic members 43 and waist elastic members 44. The leg elastic members 43 shown in FIG. 4 are bonded between the first covering sheet 41 and the second covering sheet 42 with hot melt adhesive or the like in the state where each of them is stretched (i.e., the stretched leg elastic members 43 are bonded), and the leg elastic members 43 contract to form leg gathers. The waist elastic members 44 shown in FIG. 2 are bonded between the first covering sheet 41 and the second covering sheet 42 shown in FIGS. 3 and 4 with hot melt adhesive or the like in the same way as the leg elastic members 43, and the waist elastic members 44 contract to form waist gathers. On the second covering sheet 42, the back sheet 23 of the absorber 20 is bonded with hot melt adhesive or the like.

The top sheet 21 is a nonwoven fabric made of liquid-pervious sheet material, for example, hydrophilic fibers, and the top sheet 21 immediately catches moisture of excrement from the wearer and moves the moisture into the absorbent core 22. Examples of nonwoven fabrics used for the top sheet 21 are a point-bond nonwoven fabric, air-through nonwoven fabric, spunlace nonwoven fabric and spunbond nonwoven fabric, and as hydrophilic fibers for making these nonwoven fabrics, normally, cellulose, rayon, cotton and the like are used. As the top sheet 21, a liquid-pervious nonwoven fabric made of hydrophobic fibers (for example, polypropylene, polyethylene, polyester, polyamide or nylon) where hydrophilic treatment is performed on its surface with a surfactant may be utilized.

The absorbent core 22 is formed by wrapping a mixture of hydrophilic fibers such as crushed pulp fibers or cellulose fibers and granulated absorbent polymers (e.g., SAP (Super Absorbent Polymer)) in a tissue paper, a liquid-pervious nonwoven fabric or the like, and the absorbent core 22 rapidly absorbs and retains the moisture which has passed through the top sheet 21. The tissue paper, the liquid-pervious nonwoven fabric or the like to wrap the hydrophilic fibers, is bonded to the hydrophilic fibers and the absorbent polymers with hot melt adhesive, to prevent deformation of the hydrophilic fibers and falling of the absorbent polymers (especially, falling after absorption of moisture). In the present embodiment, the absorbent core 22 includes pulp fibers and SAP.

As the back sheet 23, used is a water-repellent or liquid-impervious nonwoven fabric (for example, a spunbond nonwoven fabric, meltblown nonwoven fabric or SMS (spunbond-meltblown-spunbond) nonwoven fabric) made of hydrophobic fibers (e.g., polypropylene, polyethylene, polyester, polyamide or nylon), or a water-repellent or liquid-impervious plastic film. The back sheet 23 prevents moisture of excrement or the like which has come to the back sheet 23, from leaking out to the outer side of the main body part 2. In a case where a plastic film is used for the back sheet 23, it is preferable that a plastic film with permeability (breathability) is used, from the view point of preventing sweatiness in the absorbent product 1 and providing comfortable feeling to the wearer.

As the side sheet main body 31, used is a water-repellent or liquid-impervious nonwoven fabric (for example, a spunbond nonwoven fabric, meltblown nonwoven fabric or SMS nonwoven fabric) made of hydrophobic fibers (e.g., polypropylene, polyethylene, polyester, polyamide or nylon). For example, a polyurethane yarn, strip-like polyurethane film, yarn-like or strip-like natural rubber, or the like is used as the first elastic element 351 of the first elastic member 35, the second elastic element 361 of the second elastic member 36, and the third elastic member 37. In the present embodiment, a polyurethane yarn is used as the first elastic element 351, the second elastic element 361 and the third elastic member 37.

As the first covering sheet 41 and the second covering sheet 42 of the outer covering sheet 4, used is a water-repellent or liquid-impervious nonwoven fabric made of hydrophobic fibers, a water-repellent or liquid-impervious plastic film, or a laminated sheet of the nonwoven fabric and the plastic film in a similar fashion to the back sheet 23. It is preferable that the plastic film has permeability (breathability). Similar material to the first elastic member 35, the second elastic member 36 and the third elastic member 37 is used for the leg elastic members 43 and the waist elastic members 44. Similar material to the top sheet 21 is used for the end holding sheets 5 shown in FIG. 2.

As shown in FIGS. 3 and 4, each of the pair of side sheets 3 has a strip-like bonded part 33 and a side wall part 34. The bonded part 33 is one of two portions divided by a folding line 39 extending across almost the entire length thereof in the longitudinal direction, and the side wall part 34 is the other of the two portions. The pair of bonded parts 33 is located in the vicinity of both side edges of the main body part 2, it lies across almost the entire length thereof in the longitudinal direction, and it is bonded on the upper side (i.e., the wearer's side) of the main body part 2 with hot melt adhesive. Each side wall part 34 is continuous from the bonded part 33 at an outside edge (i.e., an edge located on the outside in the width direction) of the bonded part 33 which is the folding line 39, and on the side portion of the main body part 2, it extends across almost the entire length of the main body part 2 in the longitudinal direction.

As shown in FIG. 4, each side wall part 34 is in touch with the bonded part 33 at both end portions thereof in the longitudinal direction, and it is fixed on the bonded part 33 by heat bonding or ultrasonic bonding. In the following description, a portion fixed on the bonded part 33 in the side wall part 34 is referred to as a "side wall end part 341". Each side wall end part 341 in the pair of side wall parts 34 is indirectly fixed to the main body part 2 by the intermediary of the bonded part 33. As shown in FIGS. 2 and 3, the side wall part 34 has a standing part 342 standing up from the main body part 2 at a middle portion thereof in the longitudinal direction and it is continuous from the two side wall end parts 341. In FIG. 2, hatching lines are drawn at each side wall end part 341 of the side wall parts 34 for easy understanding of the drawing.

As shown in FIG. 4, the side wall end part 341 has a first fixed part 3411 lying inward in the width direction from the folding line 39 to be fixed to the main body part 2, and a second fixed part 3412 lying between the first fixed part 3411 and the bonded part 33 (also between the first fixed part 3411 and the main body part 2) to be fixed to the main body part 2 and spreading outward in the width direction from an inside edge of the first fixed part 3411 (that is an edge located on the inside in the width direction (i.e., an edge closer to the other side wall part 34)). The first fixed part 3411 is continuous in the longitudinal direction from a portion which is in the vicinity of a fixed edge 3421 (see FIG. 3) of the standing part 342. The tip of second fixed part 3412 is continuous from the free edge 3422 (see FIG. 3) of the standing part 342 and the second fixed part 3412 spreads with the tip directed outward.

In the side wall end part 341, the first fixed part 3411 and the second fixed part 3412 are not necessarily fixed to the main body part 2 by heat bonding or ultrasonic bonding, but the second fixed part 3412 may be bonded to the main body part 2 with hot melt adhesive, for example. In this case, hot melt adhesive is not necessarily applied between the first fixed part 3411 and the second fixed part 3412. The first fixed part 3411 is fixed to the main body part 2 together with the second fixed part 3412, since the first fixed part 3411 is continuous with the second fixed part 3412 at the inside edge.

As shown in FIG. 3, in each side wall part 34, the side sheet main body 31 has a double-layered structure, and the first elastic member 35 is bonded along the free edge 3422 of the standing part 342 with it sandwiched between two layers of the side sheet main body 31. The second elastic member 36 is bonded at a position which is between the free edge 3422 and the fixed edge 3421 (that is a part of the folding line 39) of the standing part 342 and which is away from the free edge 3422, with it sandwiched between the two layers of the side sheet main body 31. The first elastic elements 351 of the first elastic member 35 and the second elastic elements 361 of the second elastic member 36 are bonded in almost parallel with the longitudinal direction and they lie across almost the entire length of the standing part 342 in the longitudinal direction.

The first elastic member 35 and the second elastic member 36 contract to form gathers in the standing part 342.

In each side wall part 34, since each of two side wall end part 341 (see FIG. 4) has the structure described above and the first elastic member 35 is provided to the standing part 342, the standing part 342 is standing inward and upward from the fixed edge 3421 (with increasing distance from the fixed edge 3421) and in the standing part 342, a portion in the vicinity of the first elastic member 35 is lifted up in surface shape (i.e., in planar shape or in curved surface shape). Furthermore, since the second elastic member 36 is provided to each side wall part 34, an inwardly bending part 3423 (which bends inward in the standing part 342) is formed between the first elastic member 35 and the second elastic member 36. In the preferred embodiment, the inwardly bending part 3423 is curved so as to be convex upward, and a portion between the top of the inwardly bending part 3423 and the free edge 3422 is inclined downward and inward so as to come closer to the main body part 2 toward the free edge 3422. In other words, a portion of the standing part 342 being in the vicinity of the free edge 3422 is inclined downward and inward.

In the following description, the portion between the fixed edge 3421 of the standing part 342 and the top of the inwardly bending part 3423 is referred to as a "first standing portion 3424" and the portion between the top of the inwardly bending part 3423 and the free edge 3422 is referred to as a "second standing portion 3425". The first standing portion 3424 is continuous with the first fixed part 3411 of the side wall end part 341 and the second standing portion 3425 is continuous with the second fixed part 3412 of the side wall end part 341. In the first standing portion 3424, the two second elastic elements 361 of the second elastic member 36 are arranged in a direction orthogonal to the longitudinal direction (in the present embodiment, the direction is inclined relatively to the up-down direction and the width direction). In the second standing portion 3425, the two first elastic elements 351 of the first elastic member 35 are arranged in a direction orthogonal to the longitudinal direction (in the present embodiment, the direction is inclined relatively to the up-down direction and the width direction). As shown in FIG. 4, in the first fixed part 3411, the two second elastic elements 361 of the second elastic member 36 are held between the two layers of the side sheet main body 31 without being bonded thereto and in the second fixed part 3412, the two first elastic elements 351 of the first elastic member 35 are held between the two layers of the side sheet main body 31 without being bonded thereto.

In each side wall part 34 shown in FIG. 3, the third elastic member 37 is bonded along the fixed edge 3421 of the standing part 342, it lies across almost the entire length of the standing part 342, and by contraction of the third elastic member 37, a sheet part located on the outside of the absorbent core 22 in the main body part 2 (i.e., the sheet part is a portion of the top sheet 21 and the back sheet 23 where they are bonded to each other at the outside of a side edge of the absorbent core 22.) is standing upward together with the standing part 342. Therefore, a distance in the up-down direction between the standing part 342 and the main body part 2 can be made larger (i.e., a distance in the up-down direction between the top of the inwardly bending part 3423 in the standing part 342 and the top sheet 21 on the absorbent core 22 in the main body part 2 can be made larger.).

As described above, in the absorbent product 1, each side wall part 34 comprises the standing part 342, the two side wall end part 341 and the first elastic member 35, and each of the two side wall end part 341 in the side wall part 34 comprises the first fixed part 3411 and the second fixed part 3412. Therefore, the standing part 342 is standing inward and upward from the fixed edge 3421 and in the standing part 342, the portion in the vicinity of the first elastic member 35 is lifted up in surface shape. When the absorbent product 1 is worn, since the portion of surface shape in the vicinity of the first elastic member 35 in the standing part 342 comes into contact with (skin of) the wearer, it is possible to prevent the wearer from being compressed excessively (tightly) by the first elastic member 35 and to prevent excrement from the wearer, from leaking out to the outer side of the absorbent product 1 through a gap between the standing part 342 and the wearer. In addition, by a simple structure where the first fixed part 3411 and the second fixed part 3412 are provided at the side wall end part 341, the portion of the standing part 342 being in the vicinity of the first elastic member 35 can be formed in surface shape.

In the absorbent product 1, since the second elastic member 36 is provided at each of the pair of side wall parts 34, the inwardly bending part 3423 is formed at a position between the first elastic member 35 and the second elastic member 36. When the absorbent product 1 is worn, the inwardly bending part 3423 where no elastic member is provided comes into contact with the wearer to be deformed into surface shape, and a portion in the vicinity of the inwardly bending part 3423 and the first elastic member 35 (i.e., a portion on the inside of the second elastic member 36) contacts with the wearer in surface shape more certainly. It is therefore possible to more certainly prevent the wearer from being compressed excessively by the first elastic member 35 and the second elastic member 36 and to more certainly prevent excrement from leaking out to the outer side of the absorbent product 1.

In the side wall part 34, since the second standing portion 3425 (i.e., the portion of the standing part 342 being in the vicinity of the free edge 3422) is inclined so as to come closer to the main body part 2 toward the free edge 3422, the first elastic member 35 is located at a position closer to the main body part 2 than the top of the inwardly bending part 3423 (i.e., the position is away from the wearer). This can more certainly prevent the wearer from being pressed strongly by the first elastic member 35. In the absorbent product 1, the portion of the standing part 342 being in the vicinity of the free edge 3422 may be in almost parallel with the upper surface of the main body part 2, as long as the wearer is prevented from being compressed excessively by the first elastic member 35.

In the side wall part 34, since the second elastic member 36 is the two second elastic elements 361 which are arranged in a direction orthogonal to the longitudinal direction, the first standing portion 3424 on which the second elastic member 36 is located becomes surface shape and has high stiffness, and therefore the inwardly bending part 3423 is clearly formed. As the result, it is possible to easily keep the portion of standing part 342 in surface shape, where the portion is in the vicinity of the inwardly bending part 3423 and the first elastic member 35 and contacts with the wearer. Since the first elastic member 35 is the two first elastic elements 351 which are arranged in a direction orthogonal to the longitudinal direction, the portion of the standing part 342 being in the vicinity of the free edge 3422 can more easily be formed in surface shape. Furthermore, the third elastic member 37 is bonded along the fixed edge 3421 of the standing part 342 (i.e., along the folding line 39), and therefore the side sheet main body 31 can be folded easily at the folding line 39 to make the standing part 342 be standing.

Figure 5:
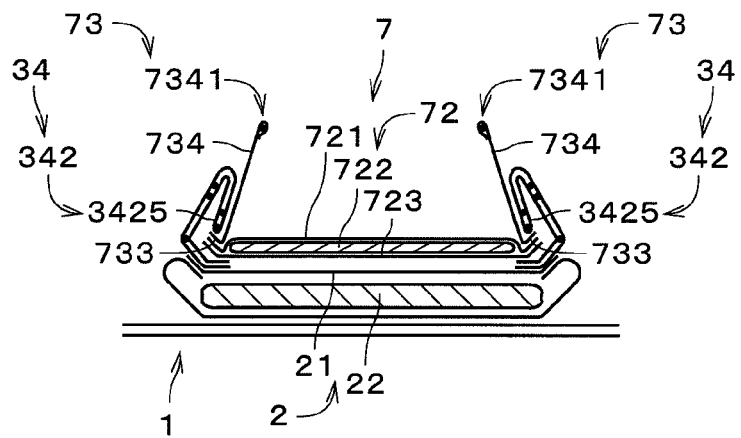
FIGS. 5 and 6 are cross-sectional views of the absorbent product and an auxiliary absorbent pad.

FIG. 5 is a cross-sectional view of the absorbent product 1 and an auxiliary absorbent pad 7 where the auxiliary absorbent pad 7 for receiving excrement from a wearer at the inner side of an exterior product to be worn by the wearer is provided (attached) at the inner side (i.e., the wearer's side) of the absorbent product 1 shown in FIGS. 1 to 4. FIG. 5 corresponds to above FIG. 3. As shown in FIG. 5, the auxiliary absorbent pad 7 has a sheet-like auxiliary absorbent main body part 72 and a pair of auxiliary absorbent side sheets 73 which is located on both side portions of the auxiliary absorbent main body part 72 (i.e., both sides in the width direction) and which extends across almost the entire length of the auxiliary absorbent main body part 72 in the longitudinal direction.

The auxiliary absorbent main body part 72 has a top sheet 721, a back sheet 723 and an absorbent core 722 which is located between the top sheet 721 and the back sheet 723. Each auxiliary absorbent side sheet 73 has an auxiliary absorbent bonded part 733 bonded on the auxiliary absorbent main body part 72 and an auxiliary absorbent side wall part 734 which extends in the longitudinal direction and which is standing up from the auxiliary absorbent main body part 72 at least at a middle portion thereof in the longitudinal direction. By this combination, excrement from the wearer is received by the auxiliary absorbent pad 7 and the excrement can be prevented from leaking out to the outer side of the auxiliary absorbent pad 7 and the outer side of the absorbent product 1.

In the absorbent product 1, the auxiliary absorbent pad 7 is located on the main body part 2 at a position between the pair of side wall parts 34, and each side portion of the auxiliary absorbent pad 7 (i.e., a portion of the top sheet 721, the back sheet 723 and the auxiliary absorbent bonded part 733 where they are bonded to one another at the outside of a side edge of the absorbent core 722) is located between the standing part 342 of each side wall part 34 and the main body part 2. Specifically the side portion of the auxiliary absorbent pad 7 is caught between the second standing portion 3425 which comes closer to the main body part 2 toward the inside and the top sheet 21 on the absorbent core 22 of the main body part 2, and therefore the auxiliary absorbent pad 7 is biased toward the main body part 2 to be fixed to the absorbent product 1 securely.

In the state where the auxiliary absorbent pad 7 is fixed on the absorbent product 1, a free edge 7341 of the auxiliary absorbent side wall part 734 projects upward at the middle portion thereof in the longitudinal direction and its top is positioned upper than the standing part 342 of the side wall part 34 in the absorbent product 1. Thus, the auxiliary absorbent side wall part 734 is tight on (skin of) the wearer. As the result, it is possible to more certainly prevent excrement from leaking out to the outer side of the auxiliary absorbent pad 7 and the absorbent product 1.

Figure 6:
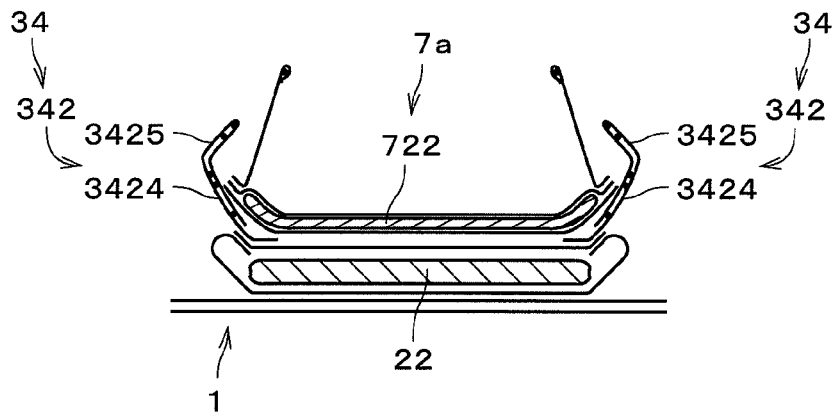

As shown in FIG. 6, when an auxiliary absorbent pad 7a where a width of the absorbent core 722 is larger than a width of the absorbent core 22 in the absorbent product 1 is provided at the inner side of the absorbent product 1, the first standing portion 3424 in the standing part 342 of each side wall part 34 is standing outward and upward and the second standing portion 3425 is standing inward and upward. Therefore, both side portions of the auxiliary absorbent pad 7a each of which lies on the outside of the absorbent core 22 in the absorbent product 1 can be held so as to be wrapped around with the pair of standing parts 342, and the auxiliary absorbent pad 7a can be fixed to the absorbent product 1 securely. As the result, it is possible to prevent excrement from leaking out to the outer side of the auxiliary absorbent pad 7a and the absorbent product 1 by a position shift of the auxiliary absorbent pad 7a or the like.

Though the preferred embodiments of the present invention have been discussed above, the present invention is not limited to the above-discussed preferred embodiments, but allows various variations.

For example, the first elastic member 35 may be one first elastic element 351 or first elastic elements 351 more than two. However, in the case where the first elastic member 35 is made to be a plurality of first elastic elements 351, the portion of the standing part 342 being in the vicinity of the free edge 3422 can more easily be formed in surface shape as described above. The second elastic member 36 may be one second elastic element 361 or second elastic elements 361 more than two in a similar fashion to the first elastic member 35. However, in the case where the second elastic member 36 is made to be a plurality of second elastic elements 361, the inwardly bending part 3423 is clearly formed and it is possible to easily keep the portion of the standing part 342 in surface shape where the portion is in the vicinity of the inwardly bending part 3423 and the first elastic member 35 and the portion contacts with the wearer, as described above.

Figure 7:
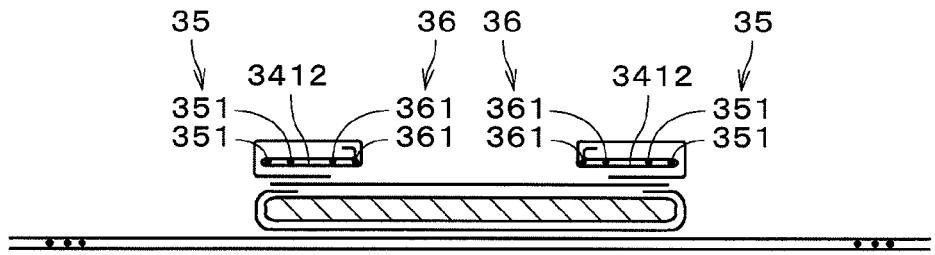
FIG. 7 is a cross-sectional view of another absorbent product.

In the side wall end part 341 shown in FIG. 4, the second elastic member 36 and the first elastic member 35 are not necessarily located at the first fixed part 3411 and the second fixed part 3412, respectively. For example, as shown in FIG. 7, two first elastic elements 351 of the first elastic member 35 and two second elastic elements 361 of the second elastic member 36 may be located at the second fixed part 3412.

Figure 8:
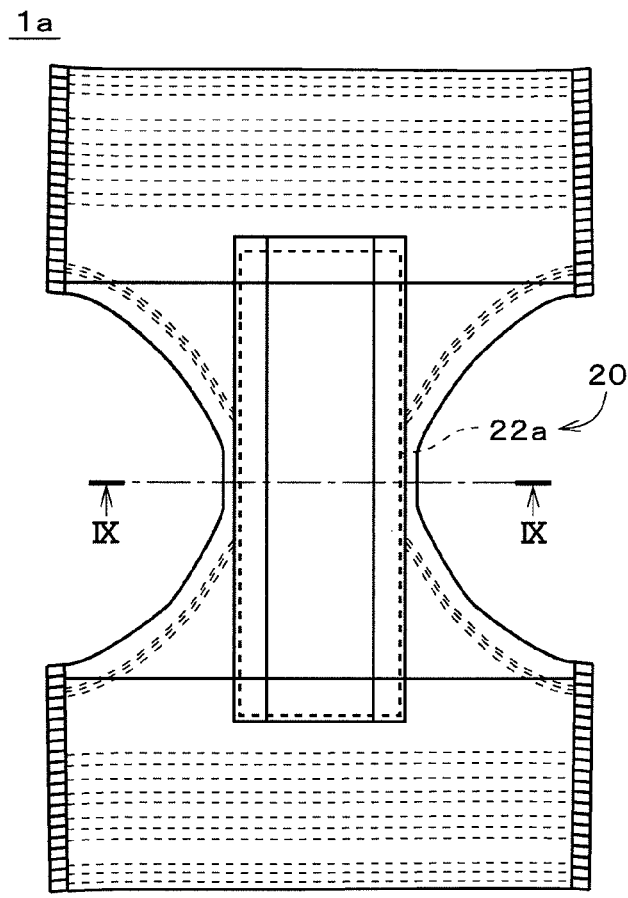
FIG. 8 is a plan view of still another absorbent product in a state where the absorbent product is developed.
Figure 9:
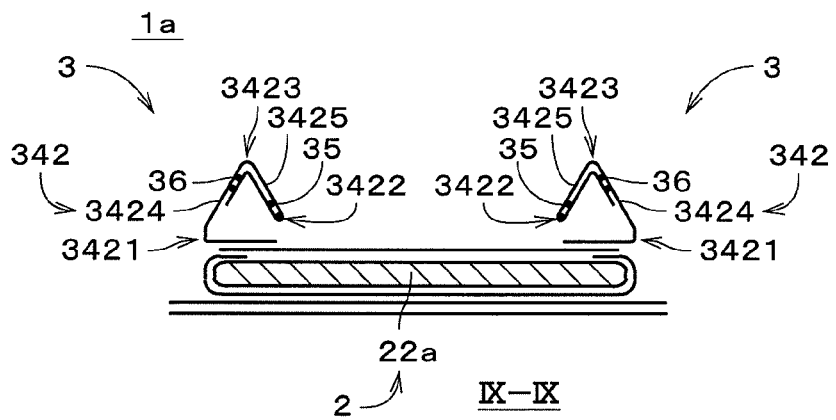
FIG. 9 is a cross-sectional view of the absorbent product.

FIG. 8 is a view showing another example of absorbent product, it is a plan view of an absorbent product 1a which is a pants-type disposable diaper in a state where the absorbent product 1a is developed and in FIG. 8, the absorbent product 1a is viewed from the wearer's side in a similar fashion to FIG. 2. FIG. 9 is a cross-sectional view of the absorbent product 1a taken along lines IX-IX in FIG. 8. As shown in FIG. 8, the absorber 20 of the absorbent product 1a has an absorbent core 22a as substitute for the absorbent core 22 formed in a form of hourglass as shown in FIG. 2 and the absorbent core 22a is almost rectangular in the plan view (i.e., the absorbent core 22a has a shape where a width in the width direction is almost equal throughout almost the entire length thereof in the longitudinal direction). Constituent elements other than that are identical to those of the absorbent product 1 shown in FIGS. 1 to 4 and the same elements are denoted by the same reference signs in the following description.

As shown in FIG. 9, in the absorbent product 1a, the fixed edge 3421 of standing part 342 in each side sheet 3 almost overlaps with the side edge of absorbent core 22a in the main body part 2. In the standing part 342, the first standing portion 3424 is standing inward and upward from the fixed edge 3421, the second standing portion 3425 is inclined inward and downward so as to come closer to the main body part 2 toward the free edge 3422, and the inwardly bending part 3423 is formed between the first elastic member 35 and the second elastic member 36, in a similar fashion to the above absorbent product 1.

In the absorbent product 1a, since the standing part 342 contacts with the wearer in surface shape in a similar fashion to the absorbent product 1, the wearer is prevented from being compressed excessively by the first elastic member 35 and the second elastic member 36, and excrement from the wearer is prevented from leaking out to the outer side of the absorbent product 1a through a gap between the standing part 342 and the wearer. In the case where the auxiliary absorbent pad 7 shown in FIG. 5 is provided at the inner side of the absorbent product 1a, since both side portions of the auxiliary absorbent pad 7 are located between the second standing portions 3425 in the pair of standing parts 342 and the main body part 2 in the same way as the absorbent product 1, the auxiliary absorbent pad 7 is biased toward the main body part 2 to be fixed to the absorbent product 1a stably.

In the above absorbent products, there may be a case where a width of the absorbent core 22 in the absorber 20 at one end in the longitudinal direction is larger than that at middle in the longitudinal direction and that at the other end in the longitudinal direction (i.e., a shape of the absorbent core 22 is like Japanese hagoita).

Structures of the above absorbent products may be utilized for various absorbent product such as an open-type disposable diaper where a portion located on the front side of a wearer and a portion located on the back side are fastened around the waistline of the wearer in wearing the disposal diaper, other than the pants-type disposable diaper.

While the invention has been shown and described in detail, the foregoing description is in all aspects illustrative and not restrictive. It is therefore understood that numerous modifications and variations can be devised without departing from the scope of the invention. This application claims priority benefit under 35 U.S.C. Section 119 of Japanese Patent Application No. 2009-216144 filed in the Japan Patent Office on Sep. 17, 2009, the entire disclosure of which is incorporated herein by reference.

REFERENCE SIGNS LIST 1, 1a absorbent product
2 main body part
3 side sheet
7, 7a auxiliary absorbent pad
21 top sheet
22, 22a absorbent core
23 back sheet
33 bonded part
34 side wall part
35 first elastic member
36 second elastic member
37 third elastic member
72 auxiliary absorbent main body part
341 side wall end part
342 standing part
351 first elastic element
361 second elastic element
734 auxiliary absorbent side wall part
3411 first fixed part
3412 second fixed part
3421 fixed edge
3422 free edge
3423 inwardly bending part
3425 second standing portion

The invention claimed is:

1. An absorbent product for receiving excrement from a wearer, the absorbent product comprising:
an outer covering sheet having leg elastic members which contract to form leg gathers;
a sheet-like main body part where an absorbent core is located between a back sheet and a top sheet, said main body part being attached on said outer covering sheet; and
a pair of side sheets located respectively on both side portions of said main body part, each of said side sheets comprising a strip-like bonded part bonded on said main body part and a side wall part which is continuous from said strip-like bonded part at an outside edge of said strip-like bonded part,
wherein said side wall parts are located respectively on both side portions of said main body part and extend in a longitudinal direction of said main body part, and each side wall part includes:
(i) a standing part standing up from said main body part at a middle portion of said side wall part in said longitudinal direction;
(ii) two side wall end parts which are both end portions of said side wall part in said longitudinal direction, the side wall end parts being fixed in a folded configuration over said main body part; and
(iii) an elastic member which is bonded to a free edge of said standing part along said free edge and which contracts to form gathers in said standing part; and
wherein each of the side wall end parts comprises:
(i) a first fixed part extending inwardly from the strip-like bonded part to an inwardly bending part which is continuous in said longitudinal direction with a portion of said standing part, said portion being in the vicinity of a fixed edge of said standing part, said first fixed part being fixed over said main body part; and
(ii) a second fixed part extending outwardly from the inwardly bending part to the free edge and disposed between said main body part and said first fixed part and being fixed over said main body part, and
wherein each of the side sheets further comprises an elastic member which extends along said fixed edge of said standing part.

2. The absorbent product according to claim 1, wherein each of said side wall parts further comprises another elastic member which is bonded to said standing part at a position away from said free edge, said another elastic member extending in a direction substantially parallel with the longitudinal direction and contracting to form gathers in said standing part, and
wherein an inwardly bending part is formed in said standing part at a position between said elastic member bonded to said free edge and said another elastic member.

3. The absorbent product according to claim 2, wherein said another elastic member is a plurality of elastic elements which are spaced apart in a direction orthogonal to said longitudinal direction and each of which extends in said longitudinal direction.

4. The absorbent product according to claim 2, wherein a portion of said standing part being in the vicinity of said free edge is almost parallel with said main body part, or said portion is inclined so as to come closer to said main body part toward said free edge.

5. The absorbent product according to claim 2, wherein said elastic member bonded to said free edge is a plurality of elastic elements which are spaced apart in a direction orthogonal to said longitudinal direction and each of which extends in said longitudinal direction.

6. The absorbent product according to claim 2, wherein a width of said absorbent core at one end in said longitudinal direction is larger than a width of said absorbent core at a middle of said absorbent core in said longitudinal direction.

7. The absorbent product according to claim 2, further comprising:
an auxiliary absorbent pad located on said main body part at a position between said pair of side wall parts, each side portion of said auxiliary absorbent pad being located between said main body part and said standing parts of said side wall parts.

8. The absorbent product according to claim 7, wherein said auxiliary absorbent pad comprises:
   a sheet-like auxiliary absorbent main body part; and
   auxiliary absorbent side wall parts which are located on both side portions of said auxiliary absorbent main body part and which extend in said longitudinal direction of said auxiliary absorbent main body part, said auxiliary absorbent side wall parts standing up from said auxiliary absorbent main body part at least at a middle portion thereof in said longitudinal direction.

9. The absorbent product according to claim 1, wherein said elastic member bonded to said free edge is a plurality of elastic elements which are spaced apart in a direction orthogonal to said longitudinal direction and each of which extends in said longitudinal direction.

10. The absorbent product according to claim 1, wherein a width of said absorbent core at one end in said longitudinal direction is larger than a width of said absorbent core at a middle of said absorbent core in said longitudinal direction.

11. The absorbent product according to claim 1, further comprising:
   an auxiliary absorbent pad located on said main body part at a position between said pair of side wall parts, each side portion of said auxiliary absorbent pad being located between said main body part and said standing parts of said side wall parts.

12. The absorbent product according to claim 11, wherein said auxiliary absorbent pad comprises:
   a sheet-like auxiliary absorbent main body part; and
   auxiliary absorbent side wall parts which are located on both side portions of said auxiliary absorbent main body part and which extend in said longitudinal direction of said auxiliary absorbent main body part, said auxiliary absorbent side wall parts standing up from said auxiliary absorbent main body part at least at a middle portion thereof in said longitudinal direction.

13. The absorbent product according to claim 1, wherein the leg elastic members are disposed outwardly of the elastic members of the side wall parts in the width direction of said main body part.

14. The absorbent product according to claim 1, wherein the outer covering sheet is disposed on an opposite side of the absorbent core from the top sheet in a thickness direction of the absorbent core,
   wherein the outer covering sheet extends outwardly beyond the side wall part of each of the side sheets in the width direction of said main body part, and the leg elastic members are disposed outwardly of the elastic members of the side wall parts in the width direction of said main body part.

* * * * *